US00PP27452P2

(12) United States Plant Patent
Uchneat

(10) Patent No.: US PP27,452 P2
(45) Date of Patent: Dec. 13, 2016

(54) CRAPEMYRTLE PLANT NAMED 'G2X133143'

(50) Latin Name: *Lagerstroemia indica*
Varietal Denomination: G2X133143

(71) Applicant: Michael S. Uchneat, Bellefonte, PA (US)

(72) Inventor: Michael S. Uchneat, Bellefonte, PA (US)

(73) Assignee: GardenGenetics LLC, Bellefonte, PA (US)

( * ) Notice: Subject to any disclaimer, the term of this patent is extended or adjusted under 35 U.S.C. 154(b) by 0 days.

(21) Appl. No.: 14/545,621

(22) Filed: May 29, 2015

(51) Int. Cl.
*A01H 5/00* (2006.01)

(52) U.S. Cl.
USPC ..... Plt./252

(58) Field of Classification Search
USPC ..... Plt./252
See application file for complete search history.

(56) References Cited

PUBLICATIONS

PLUTO Plant Variety Database Jul. 19, 2016. p. 1.*

* cited by examiner

*Primary Examiner* — Annette Para
(74) *Attorney, Agent, or Firm* — C. A. Whealy

(57) ABSTRACT

A new and distinct cultivar of Crapemyrtle plant named 'G2X133143', characterized by its relatively compact, upright to outwardly spreading plant habit; freely branching habit; bright green-colored leaves; numerous inflorescences with bright pink to rose-colored flowers; and good garden performance.

2 Drawing Sheets

Botanical designation: *Lagerstroemia indica.*
Cultivar denomination: 'G2X133143'.

BACKGROUND OF THE INVENTION

The present invention relates to a new and distinct cultivar of Crapemyrtle plant, botanically known as *Lagerstroemia indica* and hereinafter referred to by the name 'G2X133143'.

The new Crapemyrtle plant is a product of a planned breeding program conducted by the Inventor in Bellefonte, Pa. The objective of the breeding program was to develop new compact, mounding and freely-branching Crapemyrtle plants with large inflorescences, high temperature tolerance, winter hardiness and resistance to Powdery Mildew.

The new Crapemyrtle plant originated from a cross-pollination conducted by the Inventor in August, 2010 of a proprietary selection of *Lagerstroemia indica* identified as code number 8170-2, not patented, as the female, or seed, parent with *Lagerstroemia indica* 'Coral Filli', disclosed in U.S. Plant Pat. No. 14,317, as the male, or pollen, parent. The new Crapemyrtle plant was discovered and selected by the Inventor on Jan. 9, 2011 as a single flowering plant from within the progeny of the stated cross-pollination in a controlled nursery environment in Bellefonte, Pa.

Asexual reproduction of the new Crapemyrtle plant by vegetative tip cuttings in a controlled greenhouse environment in Bellefonte, Pa. since Feb. 2, 2011 has shown that the unique features of the new Crapemyrtle plant are stable and reproduced true to type in successive generations of asexual reproduction.

SUMMARY OF THE INVENTION

Plants of the new Crapemyrtle have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'G2X133143'. These characteristics in combination distinguish 'G2X133143' as a new and distinct Crapemyrtle plant:

1. Relatively compact, upright to outwardly spreading plant habit.
2. Freely branching habit.
3. Bright green-colored leaves.
4. Numerous inflorescences with bright pink to rose-colored flowers.
5. Good garden performance.

Plants of the new Crapemyrtle can be compared to plants of the female parent selection. Plants of the new Crapemyrtle differ primarily from plants of the female parent selection in the following characteristics:

1. Plants of the new Crapemyrtle are have bright green-colored leaves whereas plants of the female parent selection have pale to medium green-colored leaves.
2. Plants of the new Crapemyrtle flower earlier than plants of the female parent selection.
3. Plants of the new Crapemyrtle have bright pink to rose-colored flowers whereas plants of the female parent selection have lavender-colored flowers.

Plants of the new Crapemyrtle can be compared to plants of the male parent, 'Coral Filli'. Plants of the new Crapemyrtle differ primarily from plants of 'Coral Filli' in the following characteristics:

1. Plants of the new Crapemyrtle are more outwardly spreading than and not as upright as plants of 'Coral Filli'.

2. Plants of the new Crapemyrtle are more freely branching than plants of 'Coral Filli'.
3. Plants of the new Crapemyrtle have bright pink to rose-colored flowers whereas plants of 'Coral Filli' have coral pink-colored flowers.

Plants of the new Crapemyrtle can be compared to plants of the *Lagerstroemia indica* 'Worlds Fair', not patented. In side-by-side comparisons conducted in Bellefonte, Pa., plants of the new Crapemyrtle differed primarily from plants of 'Worlds Fair' in the following characteristics:

1. Plants of the new Crapemyrtle were more compact than plants of 'Worlds Fair'.
2. Plants of the new Crapemyrtle were more outwardly spreading than and not as upright as plants of 'Worlds Fair'.
3. Plants of the new Crapemyrtle were more freely branching than plants of 'Worlds Fair'.
4. Flowers of plants of the new Crapemyrtle were more pink in color than flowers of plants of 'Worlds Fair'.

BRIEF DESCRIPTION OF THE PHOTOGRAPHS

The accompanying colored photographs illustrate the overall appearance of the new Crapemyrtle plant showing the colors as true as it is reasonably possible to obtain in colored reproductions of this type. Colors in the photographs may differ slightly from the color values cited in the detailed botanical description which accurately describe the colors of the new Crapemyrtle plant.

The photograph on the first sheet is a side perspective view of a typical plant of 'G2X133143' grown in a three-gallon container in an outdoor nursery.

The photograph on the second sheet is a side perspective view of a typical plant of 'G2X133143' grown in a ground bed in an outdoor nursery.

DETAILED BOTANICAL DESCRIPTION

The aforementioned photographs and following observations, measurements and values describe plants grown in Grand Haven, Mich. during the summer in a polypropylene-covered shadehouse and under cultural conditions which closely approximate commercial Crapemyrtle production. During the production of the plants, day temperatures ranged from 18° C. to 27° C. and night temperatures ranged from 5° C. to 10° C. Plants were two years when the photographs and the description were taken. In the following description, color references are made to The Royal Horticultural Society Colour Chart, 1995 Edition, except where general terms of ordinary dictionary significance are used.

Botanical classification: *Lagerstroemia indica* 'G2X133143'.

Parentage:

*Female, or seed, parent*.—Proprietary selection of *Lagerstroemia indica* identified as code number 8170-2, not patented.

*Male, or pollen, parent*.—*Lagerstroemia indica* 'Coral Filli', disclosed in U.S. Plant Pat. No. 14,317.

Propagation:

*Type*.—By vegetative tip cuttings.

*Time to initiate roots, summer and winter*.—About two to three weeks at temperatures about 26° C.

*Time to produce a rooted young plant, summer*.—About four to five weeks at temperatures about 23° C.

*Time to produce a rooted young plant, winter*.—About four to five weeks at temperatures about 19° C.

*Root description*.—Fine, fibrous; white to tan in color.

*Rooting habit*.—Freely branching; medium density.

Plant description:

*Plant form and growth habit*.—Perennial shrub; relatively compact, upright to outwardly spreading plant habit; vigorous growth habit.

*Branching habit*.—Freely branching habit with about 35 lateral branches developing per plant.

*Plant height*.—About 60 cm.

*Plant diameter* (*area of spread*).—About 94 cm.

Lateral branch description:

*Length*.—About 60 cm to 65 cm.

*Diameter*.—About 5 mm.

*Internode length*.—About 1 cm.

*Strength*.—Strong.

*Aspect*.—About 15° to 45° from vertical.

*Texture*.—Smooth, glabrous.

*Color, immature*.—Close to 141D.

*Color, mature*.—Close to 200D; oldest stems, close to 142C and 200D.

Leaf description:

*Arrangement*.—Alternate to sub-opposite; simple.

*Length*.—About 5.5 cm.

*Width*.—About 3.25 cm.

*Shape*.—Elliptical.

*Apex*.—Acute.

*Base*.—Obtuse.

*Margin*.—Entire.

*Texture, upper surface*.—Smooth, glabrous.

*Texture, lower surface*.—Protruding venation; glabrous.

*Venation pattern*.—Pinnate.

*Color*.—Developing leaves, upper surface: Initially, close to 172A and becoming closer to 144A. Developing leaves, lower surface: Initially, close to 173A and becoming closer to 144A. Fully expanded leaves, upper surface: Close to 139A; venation, close to 138C. Fully expanded leaves, lower surface: Close to 146B; venation, close to 147D.

*Petioles*.—Length: About 2 mm. Diameter: About 1 mm. Texture, upper and lower surfaces: Smooth, glabrous. Color, upper surface: Close to 138C. Color, lower surface: Close to 147D.

Flower description:

*Flower type, arrangement and habit*.—Showy single ruffled flowers arranged in terminal panicles; freely flowering habit with usually about 16 flowers per inflorescence and numerous inflorescences developing during the flowering season; flowers face upright and outwardly; flowers not persistent.

*Natural flowering season*.—Plants of the new Crapemyrtle flower from June through October in Grand Haven, Mich.

*Fragrance*.—None detected.

*Inflorescence height*.—About 14.2 cm.

*Inflorescence diameter*.—About 11.5 cm.

*Flower length*.—About 4.2 cm.

*Flower diameter*.—About 4 cm.

*Flower depth*.—About 1.3 cm.

*Flower buds*.—Length: About 8 mm. Diameter: About 7 mm. Shape: Obovate. Texture: Smooth, glabrous. Color: Close to 145B overlain with close to 186A.

*Petals*.—Quantity per flower and arrangement: Six arranged in a single whorl. Length: About 2 cm. Width: About 1.4 cm. Shape: Roughly orbicular. Apex: Rounded, undulate. Base: Rounded. Margin: Entire, undulate. Texture, upper and lower surfaces: Smooth, glabrous; soft; delicate. Color: When opening, upper and lower surfaces: Close to 70C. Fully opened, upper and lower surfaces: Close to 70B and 70C; color does not fade with development.

*Sepals*.—Quantity per flower and arrangement: Six arranged in a single whorl. Length: About 9 mm. Width: About 3.2 mm. Shape: Narrowly deltoid. Apex: Acute. Base: Obtuse. Margin: Entire. Texture, upper surface: Rugose, glabrous. Texture, lower surface: Smooth, glabrous. Color: When opening and fully opened, upper surface: Close to 144B overlain with close to 176B. When opening and fully opened, lower surface: Close to 145C and 155C.

*Pedicels*.—Length: About 1.3 cm. Diameter: About 8 mm. Strength: Strong, flexible. Aspect: About 5° to 35° from stem axis. Texture: Slightly pubescent. Color: Close to 145B; striations, tinged with close to 176B.

*Reproductive organs*.—Androecium: Quantity per flower: About 29. Filament length: About 1 cm. Filament color: Close to 70D; towards the base, blended with close to 155B. Anther length: About 1 mm. Anther shape: Lanceolate. Anther color: Close to 163A; edges, close to 165A. Amount of pollen: Scarce. Pollen color: Close to 163A. Gynoecium: Quantity per flower: One. Pistil length: About 2 cm. Style length: About 1.5 cm. Style color: Close to 184D. Stigma appearance: Spherical. Stigma color: Close to 189A. Ovary: Close to 11B.

*Fruits and seeds*.—Fruit and seed development has not been observed on plants of the new Crapemyrtle.

Garden performance: Plants of the new Crapemyrtle have been observed to have good garden performance and to tolerate rain, wind and temperatures ranging from about −28° C. to about 35° C.

Pathogen & pest resistance: Plants of the new Crapemyrtle have not been observed to be resistant to pathogens and pests common to Crapemyrtle plants.

It is claimed:

1. A new and distinct Crapemyrtle plant named 'G2X133143' as illustrated and described.

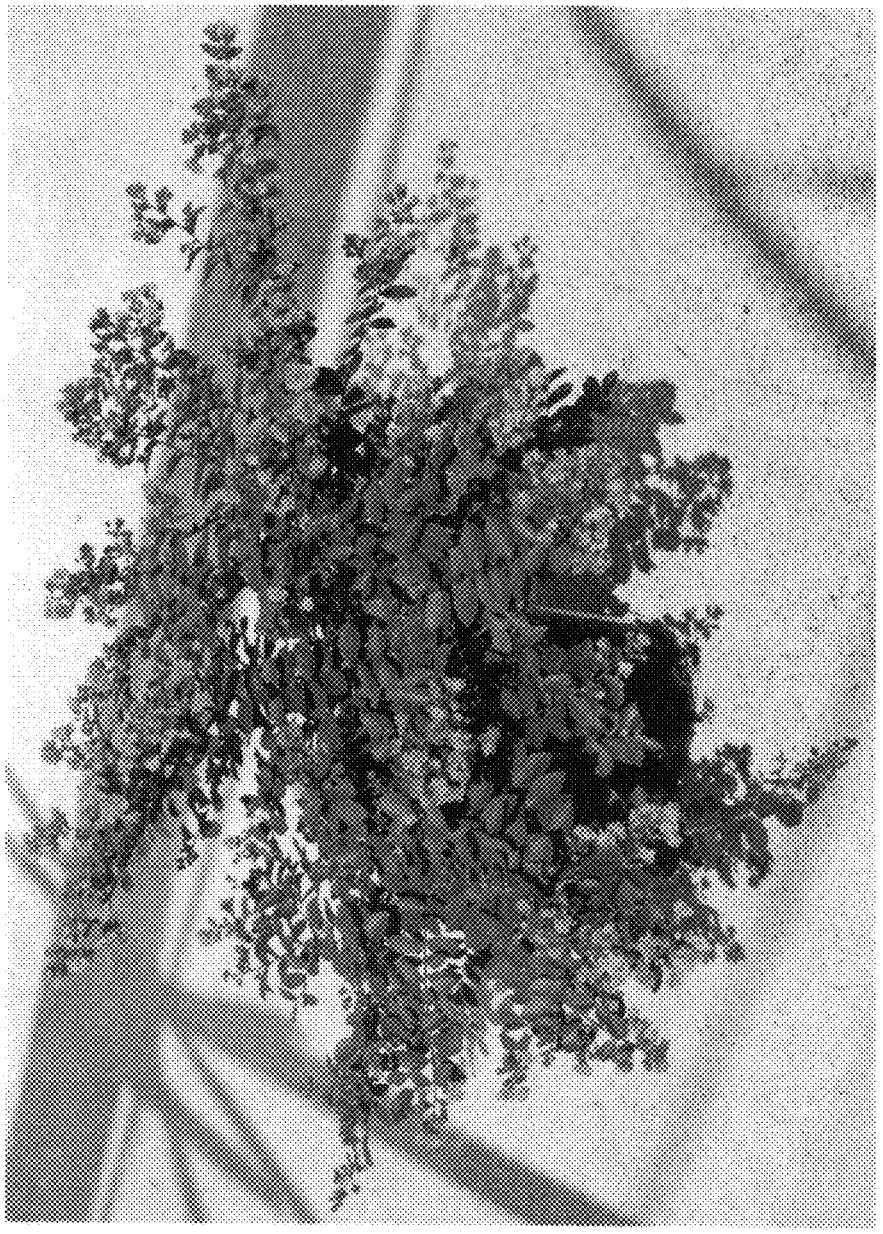

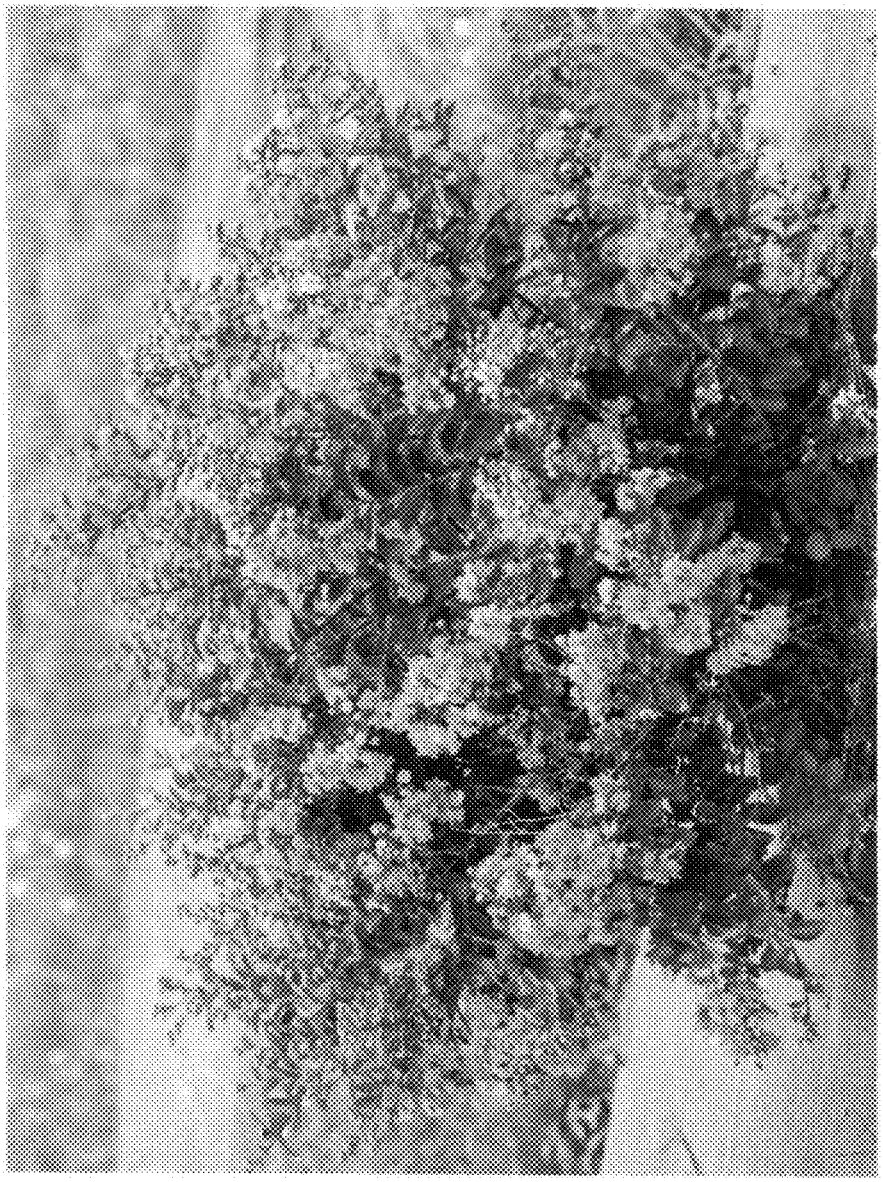

* * * * *